United States Patent [19]
Jouan et al.

[11] 3,987,165
[45] Oct. 19, 1976

[54] PRODUCT FOR PREVENTION AGAINST OPHIOBOLUS TAKE-ALL IN CEREALS AND THE LIKE

[75] Inventors: Bernard Jouan; Jean-Marc Lemaire, both of Pace, France

[73] Assignee: Institut National de la Recherche Agronomique, Paris, France

[22] Filed: Sept. 25, 1974

[21] Appl. No.: 509,218

[30] Foreign Application Priority Data

Sept. 27, 1973 France .............................. 73.34619

[52] U.S. Cl. .................................. 424/93; 195/53; 195/54; 424/195
[51] Int. Cl.² ................. A61K 37/00; A61K 35/84; C12K 1/00
[58] Field of Search ................. 424/93, 195, 92, 89; 195/53, 54

[56] References Cited
OTHER PUBLICATIONS

Shipton et al., Chem. Abst. vol. 79 (1973), p. 4271t.

Primary Examiner—Sam Rosen
Attorney, Agent, or Firm—Donald D. Jeffery

[57] ABSTRACT

The invention relates to a product for the treatment of cereal crops against the effect of *Ophiobolus graminis* which product comprises a culture of an abnormal homogeneous strain of *Ophiobolus graminis* carried on a divided support medium.

8 Claims, 4 Drawing Figures

PRODUCT FOR PREVENTION AGAINST OPHIOBOLUS TAKE-ALL IN CEREALS AND THE LIKE

This invention relates to a product for controlling take-all in cereal crops, to a process for preparing this product and to an application of this product.

BACKGROUND OF INVENTION

Take-all is a serious disease of cereals (wheat, barley, rye) which reduces the quality of the crops and the yields. In addition, it is an extremely difficult disease to detect because it can be confused with physiological shrivelling or with premature ripeness.

The agent responsible for this cryptogamic disease is *Ophiobolus graminis*. This fungus attacks and cankers both the radicular systems and the base of the stems of the cereals on which perithecia can form. The inoculum keeps well year after year, more especially in sensitive graminaceae, new growths and harvesting residues of diseased cereals. Accordingly, the infestation of a field persists for several years following an initial inoculation.

It would seem that dissemination of the inoculum during the primary infestation is caused by the transport of particles of soil or harvesting residues by agricultural machinery or even by wind. In any one field the parasite progresses from plant to plant either by the aerial route through ascospores or by the subterranean route through the mycelium. So far as the spread of the disease in a field is concerned, root-by-root propagation is the most prevalent form of propagation, its rate being determined both by the type of soil (extremely high in light, aerated and alkaline soil, becoming lower in heavy, acid soil or high-humus soil) and by the planting density.

Hitherto, various methods have been proposed for controlling this disease, including for example rotation cropping, acceleration of the process by which harvesting residues are degraded by cultural methods in order to restrict persistence of the inoculum, development of a microflora to counteract the effect of the fungus, sowing in seed holes to restrict propagation of the disease, and above all rotation cropping in which the growing of sensitive cereals is not often included.

Unfortunately, none of these processes is completely effective, rather are they only palliatives whose object is to reduce the intensity of the disease and above all its effects, but not to treat it.

Accordingly, it is necessary to find a process for treating take-all from which immediate and substantial results can be obtained. The principal solutions considered in the past would appear to be either of a chemical nature (using phytochemical agents) or of a botanical nature by obtaining varieties of cereals resistant to Ophiobolus graminis, but unfortunately none of these possibilities would appear at present to be really practicable. Thus, if for example certain varieties of cereals are more likely to grow new roots, none of them would have a resistance level that could be exploited within the range of selection.

SUMMARY OF THE INVENTION

The present invention is the outcome of a study of the evolution of the disease and of the biological cycle of the parasite which will be summarised hereinafter in order to make the invention easier to understand, but which in no way limits the invention.

The most unpleasant characteristic of take-all is that the parasite responsible, which is widespread in all wheat-producing countries, persists in a field for the first few years following an initial infestation and invariably causes heavy losses of yield when wheat is grown for a second or third time on the same area of land. This characteristic prevents intensive rotation cropping of the kind which farmers in high-growth areas are seeking to undertake.

Accordingly, it is essentially in the perspective of intensive rotation cropping that the present invention has its place.

A time study of the disease has enabled its different phases to be determined. Thus, when wheat is continuously grown on an area of land favourable to attacks of take-all, an infestation or latence phase, which we shall call phase A, is initially observed and can last for a perid of 1 to 3 years. During this phase, the field is more or less healthy and there is no sign of any drop in yield. The inoculum then multiplies vigorously and the intensity of the disease increases to an ultimate stage which, depending upon the type of soil, is reached after 2 to 4 years, This phase will be referred to hereinafter as phase B or the phase of maximum intensity of the disease. During the following years, however, the disease undergoes a natural regression to the point where it stabilises below the damage threshold. This phase will be referred to hereinafter as phase C or the immunity phase (this designation will be explained hereinafter). These various phases are illustrated in the form of a graph in FIG. 1 in which the time in years is recorded on the abscissa and the intensity of the disease on the ordinate. The marking system of 0 to 100 used for the intensity of the disease is easy to understand if it is known that, for a disease intensity of 100, the crop is completely destroyed, i.e. substantially non-saleable. The tests illustrated were carried out in Brittany and enabled yields of more than 45 hundredweight per hectare to be obtained after 14 years of wheat growing.

Unfortunately, this method of natural control has one very serious disadvantage, namely that it involves a loss of crop.

The phenomenon of regression of the disease observed in phase C is probably explained in part by changes in the microbial equilibria in a direction which adversely affects the parasite.

However, the main explanation of the phenomenon of regression would appear to be the appearance of abnormal strains of *Ophiobolus graminis* which have lost their pathogenic power, and Applicants have found that it is possible to protect the cereals against attacks of take-all and to reduce contagion by using a product containing these abnormal strains.

Accordingly, the invention relates to a product intended for controlling take-all consisting of a culture of an abnormal, homogeneous strain of Ophiobolus graminis on a divided supporting medium, said abnormal homogeneous strain being such that, when subcultured in a non-divided homogeneous culture medium, it does not produce during its development the appearance of concentric growth zones under light. Supporting media suitable for use in accordance with the invention preferably include grains of cereals, straw, flour and cereal residue. In one preferred embodiment of the invention, the supporting medium consists of grains of previously killed cereals. The invention covers both the products in which the abnormal strain is living and the products in which the abnormal strain is dead.

The invention also relates to a process for preparing the above-mentioned product, distinguished by the fact that strains of Ophiobolus graminis containing at least one abnormal strain are cultured on suitable culture media, the abnormal strains are identified after growth by observing their appearance under light, the normal strains showing concentric growth zones whilst the abnormal strains show uniform growth, samples of the abnormal strains are taken and, optionally, subcultured on a new medium so as to obtain a homogeneous culture, and finally are cultured on a divided supporting medium.

In one preferred embodiment of the process according to the invention, the strains to be selected are taken from cereals growing in an intensive rotation-cropping field at a time when they have undergone the maximum intensity phase of take-all, i.e. are only left with very slight signs of attack.

According to the invention, it is of course possible to use abnormal strains obtained by another process.

The invention also relates to the application of the product described above, this application being distinguished by the fact that the product is mixed with seeds during seeding, or even by the fact that this product is distributed in the field by scattering. Although it is possible to use any suitable means by which the product according to the invention can be incorporated in the soil, the preferred embodiment comprises coating the seeds with a non-phytotoxic adhesive such as methyl cellulose or polyvinyl pyrrolidone (PVP), and then bringing the seeds thus coated into contact with the product according to the invention. The particular advantage of this embodiment is that it increases the quantity of product per hectare and improves contact between the plants and the hypovirulent strain.

Another interesting application of the product according to the invention comprises infecting the field to be treated with fungi related to Ophiobolus graminis, such as *Phialophora radicicola* isolated from various, optionally cultivated gramineea.

In the context of the invention, an "abnormal homogeneous strain" of Ophiobolus graminis is a strain which, by culture on a homogeneous non-divided medium, does not produce the phenomenon known as "zonation" under light, i.e. it is not possible to distinguish concentric growth circles such as appear when a normal strain of Ophiobolus graminis is cultured. These strains generally show a marked hypovirulence character, which explains why they are occasionally referred to hereinafter as "hypovirulent strains", are much more fragile than normal strains, keep relatively poorly in gelose-containing nutrient media, with the result that their preservation involves frequent subculturing, in addition to which they no longer form perithecia. Although the presence of virus has been noted in almost all abnormal strains, determination of the virus is occasionally difficult, if not completely impossible, because it has not been able to be localised in all the abnormal strains, and it is now no longer certain whether it is the principle agent behind the drop in virulence of abnormal strains. Nevertheless, all the purified virus-affected strains are hypovirulent strains.

Culturing of the strains on divided supporting media does not involve any difficulty, the parasite growing readily, especially in cases where the divided support emanates from cereals. Although conservation in a completely artificial medium does involve certain difficulties due to the fragility of abnormal strains, it is nevertheless possible and, accordingly, falls within the scope of the present invention.

DESCRIPTION OF PREFERRED EMBODIMENTS

Figure 1:
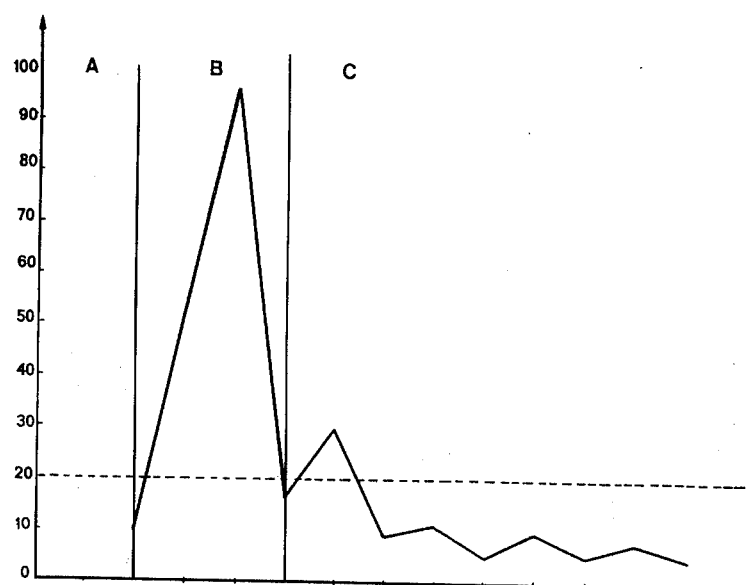
Figure 2:
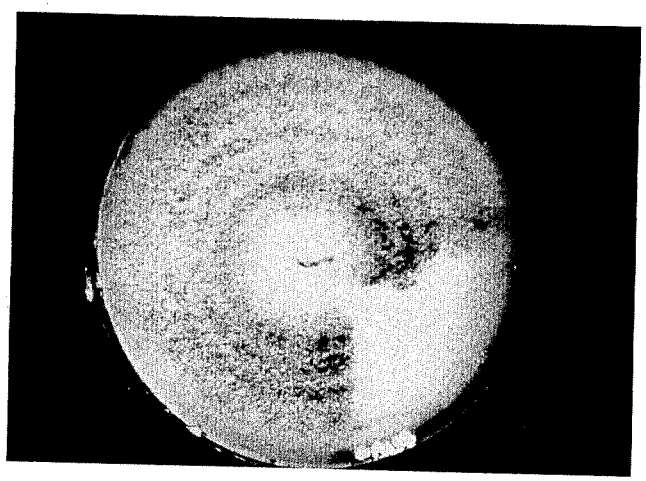

In one preferred embodiment of the process according to the invention, a slightly cankered root sample is taken from wheat in phase C of its attack by take-all and from a plant which appears to have resisted that attack, the abnormal strains only very rarely altering the base of the stems, and is cultured in nutrient media of the kind commonly encountered in microbiology. The strain which develops can be one of three types:

homogeneous with concentric growth zones which appear under light (normal homogeneous strain);

homogeneous without the appearance of concentric growth circles under light (abnormal homogeneous strain);

heterogeneous with appearance of circular pigmented sectors differing in colour and generally lighter, these sectors corresponding to the development of an abnormal strain (cf. photograph, FIG. 2).

The photograph of FIG. 2 shows this third type of development. This photograph clearly shows a dark circular sector showing the phenomenon of "zonation", i.e. darker concentric growth circles and a lighter, pigmented circular sector which corresponds to the development of an abnormal strain. Sampling of this pigmented sector, subcultured on another culture medium, generally leads to a homogeneous culture without the appearance of concentric growth zones under light. The abnormal homogeneous strain thus obtained is then cultured to obtain a product according to the invention. To this end, the supporting medium is preferably used in a fairly thick form with numerous interstices so that the mycelium can develop and be protected. Thus, in the following Examples, the product according to the invention was prepared by filling a milk bottle to one third of its volume with grains of barley, placing the whole in an autoclave to sterilise it and to kill the grains of barley, adding a little water and inoculating the supporting medium thus obtained.

This culture of an abnormal strain on a divided medium is then inoculated in the soil by any suitable method, in particular by spreading over the soil during sowing (or after harvesting a previous crop of wheat or during the sowing of catch-crop wheat) of an abnormal strain grown on grains of barley, by powdering seeds during sowing with a powder either consisting of grains of barley colonised by the abnormal strain or obtained from a culture multiplied on an optionally gelose-containing nutrient medium.

The product according to the invention has a double effect: it has a forearming action on fields which have never been subjected to attack by take-all by directly placing them as it were in phase C of the disease described above, in addition to which it restricts contagion and enables the disease to be brought under control fairly rapidly.

The forearming effect was demonstrated by the following three tests:

FIRST TEST

In vitro a seedling of wheat is contacted with a selected abnormal strain by the process described above for about 1 week at temperature of 20° C. This seedling is then subcultured in a medium heavily infested with an extremely virulent strain, after which there is a very distinct decrease in the attack in relation to the control which had not been previously contacted with an abnormal strain.

SECOND TEST

Figure 4:
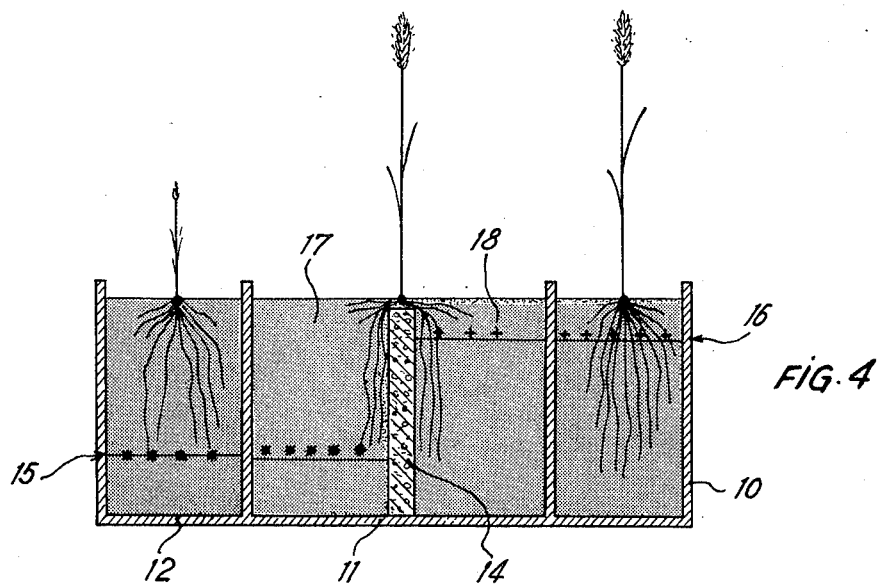

This test carried out with a VPM wheat multiplied by harvesting (obtained from Aegilopse ventricosa) and diagrammatically illustrated in FIG. 4 is the following: of three growing boxes 10, 11 and 12, the box 11 is divided into two compartments by a small concrete wall which isolates two parts of the box. In box 12 and in compartment 17 of box 11, soil is introduced to level 15, the surface is inoculated with a highly virulent strain, after which box 12 and compartment 17 are completely filled. In box 10 and compartment 18 of box 11, soil is introduced up to a level 16, this level being higher than the aforementioned level 15, the surface is infested with an abnormal strain, after which box 10 and compartment 18 of box 11 are completely filled. One seed is then planted in box 12, one seed in box 11 above the concrete wall. At the end of growth, the wheat plants in boxes 10 and 11 are found to be identical in appearance and healthy, whilst the wheat plant in box 12 is virtually dead. This result can be explained as follows: during the development of the roots of the wheat plant in box 11, the roots grow almost equally on either side of the concrete wall 14. After having reached a certain stage of development, the root system in compartment 18 is attacked by the hypovirulent strain with which the surface 16 has been inoculated. This attack forearms the plant as a whole so effectively that, when the root system in compartment 17 reaches the highly virulent strain, the plant is not attacked. Accordingly, the product according to the invention effectively forearms the plant in a general manner.

THIRD TEST

Figure 3:
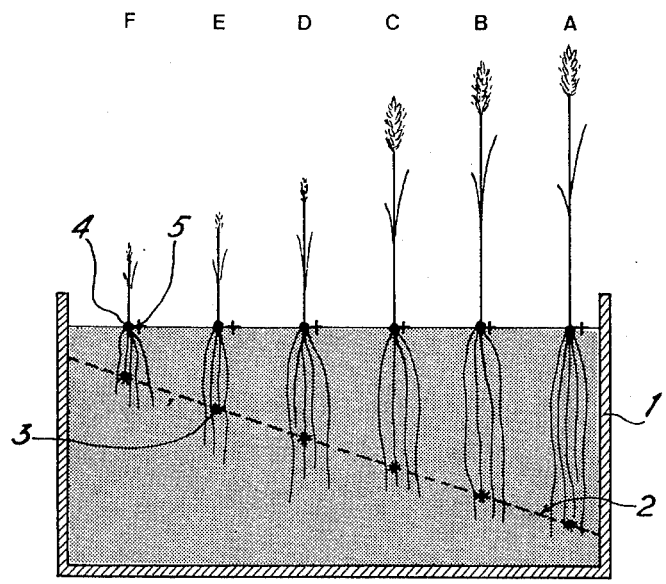

This test, diagrammatically illustrated in FIG. 3, demonstrates once again the forearming effect obtained by the process according to the invention and, above all, the importance of rapid, preventive action in the treatment of take-all. A sloping layer of soil 2 in a growing box 1 is inoculated at regular intervals with highly virulent strains (denoted by asterisks), after which this sloping layer of soil is covered with more soil to make its surface horizontal. Seeds of wheat, such as 4, are planted substantially at the level of the highly virulent strains, being treated by the product according to the invention in the form of grains of barley, such as 5, colonised by an abnormal strain. At the end of growth, the appearance of the corn obtained in the growing box is noted. Whereas plants A, B and C are more or less healthy, plants E and F are virtually dead. This is explained by the fact that the forearming effect did not have sufficient time to develop in plants E and F before the highly virulent strains attacked the root system, whereas in the case of plants A and B in particular the forearming effect did develop and when the root system reached the highly virulent strains, they remained without any effect.

Field tests have confirmed the results obtained in laboratory tests and have shown other features and advantages of the invention.

Thus, a first group of 10 tests carried out in 1971/1972 showed that the treatment of wheat plants by the product according to the invention did not produce any fall in yield (most of the tests were carried out in areas where take-all does not cause any damage during the first growth of the wheat).

In one case, yield was even found to have been increased by about 400 kg per hectare (i.e. from 2,400 to 2,800 kg per hectare). It would seem that this increase in yield was attributable above all to a limitation of the extent of the primary infection by forearming the corn treated by the product according to the invention. However, the effect of the treatment will only be clear 1 or even 2 years after incorporation of the abnormal strain.

The increase in yield in the plots treated with the product according to the invention appeared very general, both in the year of treatment and in the following years.

Thus a test carried out on wheat of the Kavkaz variety sown on the Oct. 15, 1972, the fieldhaving been inoculated with a highly pathogenic strain at a rate of 1 g of inoculum per 10 square meters and only a part having been treated with a virus-affected hypovirulent strain at a rate of 100 g of inoculum per 10 square meters, produced the following results in terms of yield:

5,000 kg per hectare for the control, and 5,500 kg per hectare for the treated wheat, the figures corresponding to averages of 4 repetitions.

In another test, in which a field had been partly treated in 1971 at the rate of 100 kg/ha of a hypovirulent strain, take-all appeared naturally in 1972. Wheat of the Champlein variety sown in this field on the Dec 9, 1972 produced the following yields in 1973;

3,250 kg per hectare for the untreated control plot, and 3,730 kg per hectare for the treated plot.

In a field test, it was found that the propagation of the disease from plant to plant in a naturally infested soil was distinctly reduced by infesting the soil with the product according to the invention. In this test, the seeds were also sown in seed holes with the object of containing the disease from primary centres of infection. However, treatment with the abnormal strain did not bring about any improvement in the case of seed-hole sowing, which is normal insofar as the two treatments act on the same development factor of take-all.

In two tests, one of which was carried out on barley in Morbihan by the I.T.C.F., and the other on spring wheat in Rheu by the I.N.R.A., a centre of infection was artificially created with an extremely virulent strain, all the plots being treated with the product according to the invention.

In the two tests, it was found that, although at the very centre of the infection the treatment produced hardly any reduction in the disease, it had nevertheless prevented the disease from spreading from the centre of infection towards the rest of the plot, whereas in the control plots propagation had taken place.

The following Table shows the results obtained during the test conducted by I.N.R.A.:

Effect of a treatment with a virus-affected strain on the propagation of take-all from an artificially created centre of infection (expressed in cm):

| Treatments | Visual observations during growth 1st observation | 2nd observation | Observations of the radicular system |
|---|---|---|---|
| 1 | 54 | 80 | 70 |
| 2 | 42 | 78 | 78 |
| 3 | 31 | 61 | 30 |
| 4 | 27 | 46 | 20 |
| 5 | 41 | 52 | 63 |

1 — First untreated control
2 — Second untreated control
3 — General treatment during sowing at a rate of 100 kg/ha of a virus-affected strain (No. 612)
4 — General treatment during sowing at a rate of 100 kg/ha of a mixture of two virus-affected strains (911 and 511-2)
5 — Treatment of seedlings at a rate of 500 g/cwt of a powder containing strain No. 911.

The above tests demonstrate the harmlessness of treatment with the product according to the invention, and the fact that, in cases where infestation by a virulent strain exists, the product enables propagation of the disease to be contained.

The object of the following tests was to demonstrate that the beneficial effect of the treatment by the process according to the invention continues for the following years.

Thus, a test carried out at the Rheu Establishment showed that a wheat initially attacked by a hypovirulent strain is not subsequently attacked by a highly virulent strain.

This test thus confirms the results of tests, 1, 2 and 3 reported above.

A final test demonstrated the fact that the contagion between two plots, one infested with a virulent strain and the other with a hypovirulent strain, is in favour of the hypovirulent strain, which represents another advantage of the product according to the invention.

Thus, 6 plots were treated in the following manner:
1. non-inoculated control plot,
2. control plot inoculated with a highly pathogenic strain,
3. control plot inoculated with a hypovirulent virus-affected strain,
4. plot treated with a hypovirulent strain, adjoining plot 5,
5. plot treated with a highly pathogenic strain, adjoining plot 4,
6. plot infested simultaneously with both strains.

The results obtained are set out in the following Table. The figures quoted are approximate assessments which, for values from 1.5 to 1.6, correspond to substantially healthy plots, and for values of the order of 0.5 or less to extremely sick plots.

TABLE 1

| | 1970–1971 | 1971–1972 | 1972–1973 approximate | 1973–1974 | |
|---|---|---|---|---|---|
| 1 | 1.4 | 1.6 | 1.3 | 1 | (48) |
| 2 | 0.08 | 0.5 | 0.5 | 0.7 | (27) |
| 3 | 1.4 | 1.5 | 1.5 | 1.7 | (74) |
| 4 | 1.2 | 1.5 | 1.5 | 1.6 | (69) |
| 5 | 0.07 | 1.2 | 1.3 | 1.7 | (72) |
| 6 | 0.40 | 0.9 | 1.5 | 1.7 | (73) |

The figures in brackets corresponding to the 73–74 season are yields in hundredweight per hectare.

The following conclusions may be drawn from these figures: Plot No. 1 begins to become very ill with a significant drop in yield in 73–74. Plot No. 2 gives hardly any crop over the 4 year period, whilst plot No. 3 gives yields similar to those of plot No. 1 in 1970, and actually shows a significant increase in yield in 1973–1974, as do plots Nos. 4, 5 and 6. Plot No. 5 recovers through contagion from plot No. 4, whilst plot No. 4 has not suffered from the proximity of plot No. 5. Plot No. 6 has become completely healthy.

It should be noted that, in the tests reported above, the inoculations with highly virulent strains are massive inoculations which are hardly ever encountered in the natural state, and also that the virulent strains used are strains selected for their virulence which, to some extent, explains the drops in yield observed in plot No. 6 treated with both strains.

The tests conducted to determine the improvements obtained during the actual year of treatment, especially in dependence upon the variety of wheat used, produced the following results:

A wheat which has been grown under aseptic conditions on a gelose-containing medium in a Petri dish and whose roots have been inoculated with a hypovirulent strain, releases in the gelose after a period of 2 to 3 days a substance which inhibits the growth of a pathogenic strain of Ophiobolus graminis from a distance (2 cm).

This phenomenon is variety-related. It is much more pronounced with certain lines belonging to the V.P.M x moisson varieties than with control varieties such as Joss.

A large number of field tests demonstrated that the controls adjacent treated plots benefited from the effect of the hypovirulent strains, and that this beneficial effect was associated with the variety, as shown in Table 2 below.

Table 2

| Type of treatment | Dose Kg/ha | Cereal previously grown | Variety of wheat | Number of plots treated | control | Yield in cwt/ha treated | control | Percentage increase in yield |
|---|---|---|---|---|---|---|---|---|
| open-air | 80 | maize | Champlein | 12 | 20 | 41 | 31 | +25 |
| open-air | 80 | wheat | Joss | 24 | 24 | 51 | 45 | +15 |
| open-air | 80 | wheat | V.P.M. × moisson 9 | 12 | 12 * | 69 | 49 | +43 |
| open-air | 80 | wheat | V.P.M. × moisson 9 | 27 | 12 * | 64 | 49 | +30 |
| open-air powdering of seedlings | 120 10 6 | wheat | V.P.M. × moisson 9 | 54 | 12 * | 79 | 49 | +60 |
| open-air powdering of seedlings | 50 6 | | V.P.M. × moisson champlein | 11 | 12 | 37 | 30 | +23 |

Table 2-continued

| Type of treatment | Dose Kg/ha | Cereal previously grown | Variety of wheat | Number of plots treated | Number of plots control | Yield in cwt/ha treated | Yield in cwt/ha control | Percentage increase in yield |
| --- | --- | --- | --- | --- | --- | --- | --- | --- |
| open-air powdering of seedlings | 50 6 | | Rex | 12 | 12 | 30 | 30 | 0 |

* The plots in question here are the twelve plots which on three earlier occasions had been used as reference plots.

Remarks:

In view of the previously reported observation, it was necessary to carry out the various tests by separating the treated plots from the control plots in terms of space in order to avoid any propagation of the beneficial effect of the treatment according to the invention.

Among the results reported in this Table, the results observed with the varieties V.P.M. × moisson are particularly significant, leading to increases in yield of around 60 % which is considerable and represents another advantage of the product and process according to the invention.

Finally, field tests carried out on plots consisting of untreated lines and of lines treated with 80 Kg/ha produced the following results:

| Varieties of lines | Number of repetitions | Percentage increase in the weight of the heads per plot |
| --- | --- | --- |
| Capitol | 3 | + 14 |
| Mironovskaia 808 | 3 | − 21 |
| Kavkaz | 9 | + 75 |
| Aurora | 9 | + 48 |
| V.P.M. × moisson 4122 | 9 | + 42 |
| V.P.M. × moisson 4123 | 6 | + 2 |
| V.P.M. × moisson 8. 3.11 | 3 | + 10 |
| V.P.M. × moisson 9.5.1 | 6 | + 18 |
| V.P.M. × moisson 9 9 1 | 6 | + 44 |

This table again demonstrates the favourable effect of the compound according to the invention in improving the yields of certain varieties of wheat. Naturally, the results quoted are only preliminary results which do not allow definitive conclusions to be drawn, although it is highly probable that the variety of wheat treated has a notable effect on the effectiveness of the treatment process from the 1st year of its application.

It should be noted that, in the tests described above, the inoculations with highly virulent strains are massive inoculations of the kind rarely encountered in the natural state, and also that the virulent strains used are strains selected for their virulence which partly explains the drops in yield observed in plot 6 treated with the two strains at the same time.

Finally, it should be pointed out that when wheat is grown in a soil for several years afterwards, and that the damage attributable to take-all has become negligible by a natural process following the year of very heavy attack, it becomes virtually impossible to successfully superinfest the soil with a virulent strain, even with very large doses of inoculum. When the evolution of the superinfestation is monitored, it is found that some wheat plants disappear at a very early stage (in the month following sowing), although as a result the coronary roots are formed and the wheat regains strength. It would seem as if the hypovirulent strain naturally present in the soil contaminates the highly pathogenic strain introduced. In this case, it is no longer a question of a forearming effect because the virulent strain introduced into the seed bed attacks the wheat from germination onwards so that, in all probability, it is more a question of a rapid loss of virulence in the strains introduced, and it is possible that this rapid loss of virulence is associated with contagion from the strains present in the soil.

Thus, the product according to the invention is a very effective means of controlling take-all in wheat of any variety and, principally, in the varieties VPM x Moissons and Kazkaz, both by virtue of its persistent forearming effect and by virtue of the fact that it limits contagion.

What is claimed is:

1. A product intended for the treatment of take-all in cereals, which product comprises a culture of an abnormal homogeneous strain of Ophiobolus graminis on an interstices — containing support medium suitable for sustaining the growth of an abnormal homogeneous strain of the organism, the abnormal homogeneous strain being such that, when subcultured on a non-divided culture medium and after growth, it does not produce any concentric growth circles under light.

2. A product as claimed in claim 1, wherein the supporting medium is selected from grains of cereals, straw, flour and cereal residue.

3. A product as claimed in claim 1, wherein the supporting medium consists of grains of previously killed cereals.

4. A product as claimed in claim 1, wherein the abnormal strain is dead.

5. A product as claimed in claim 1, wherein the abnormal strain is living.

6. A product as claimed in claim 1, wherein the abnormal strain is a virus-affected strain.

7. A process for the treatment of take-all in cereals wherein the soil is treated before sowing by scattering thereon and admixing with the cereal seed a culture of an abnormal homogeneous strain of Ophiobolus graminis on an iterstices — containing support medium suitable for sustaining the growth of an abnormal homogeneous strain of the organism, said abnormal strain being characterised by failure to produce concentric growth circles under light when subcultured on a non-divided culture medium.

8. A process as claimed in claim 7, wherein the product is used in combination with the conidian form of Ophiobolus graminis, namely Phialophora radicicola.

* * * * *